US00PP28055P3

(12) United States Plant Patent
Orard

(10) Patent No.: US PP28,055 P3
(45) Date of Patent: May 30, 2017

(54) CLIMBING ROSE PLANT NAMED 'ORALODSEM'

(50) Latin Name: *Rosa hybrida*
Varietal Denomination: ORAlodsem

(71) Applicant: Early Morning LLC, Pomona, CA (US)

(72) Inventor: Pierre Orard, Feyzin (FR)

(73) Assignee: Early Morning LLC, Pomona, CA (US)

( * ) Notice: Subject to any disclaimer, the term of this patent is extended or adjusted under 35 U.S.C. 154(b) by 60 days.

(21) Appl. No.: 14/544,327

(22) Filed: Dec. 23, 2014

(65) Prior Publication Data
US 2016/0183420 P1 Jun. 23, 2016

(51) Int. Cl.
*A01H 5/02* (2006.01)

(52) U.S. Cl.
USPC ..... Plt./109

(58) Field of Classification Search
USPC ..... Plt./109
See application file for complete search history.

*Primary Examiner* — Anne Grunberg
(74) *Attorney, Agent, or Firm* — McKee, Voorhees & Sease, PLC

(57) ABSTRACT

A new variety of Climbing rose suitable for garden decoration, having flowers of burgundy purple striped with cream yellow coloration overlaid with a coral orange blush.

1 Drawing Sheet

Classification: The present invention relates to a new *Rosa hybrida* plant.

Variety denomination: The new plant has the varietal denomination 'ORAlodsem'.

BACKGROUND OF THE INVENTION

This invention relates to a new and distinct variety of Climbing Rose. It has as its seed parent the variety known as 'ORAstricap' (not patented) and a non-disseminated seedling of my creation as its pollen parent with the following genetic origin (MEIronsse×HARzazz). It was hybridized by Pierre Orard, Au Jardin des Roses, Etablissements Horticoles Orard, 56 route de Lyon, 69320 Feyzin, France.

SUMMARY OF THE INVENTION

Among the features which distinguish the new variety from other presently available and commercial rose cultivars known to the inventor are the following combinations of characteristics: its very unusual flowers of burgundy purple striped with cream yellow coloration overlaid with coral orange blush, its many hairs on the peduncle and its very glossy large foliage. The plant has a spreading climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'ORAlodsem' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'ORAstricap' by the following combination of characteristics: whereas 'ORAlodsem' bears double flowers (about 21 to 29 petals) of burgundy purple striped with cream yellow coloration overlaid with a coral orange blush, 'ORAstricap' bears semi-double flowers of smoked orange striped cream coloration with Significantly lesser petalage (about 9 to 16 petals). The new variety is classified as a Climbing rose with a spreading climbing growing habit with canes about 300 cm. to about 350 cm. in length, whereas the seed parent is classified as Shrub rose with a significantly shorter growing habit (about 120 to about 150 cm. in height).

The new variety may be distinguished from its pollen parent, a non-disseminated seedling of my creation by the following combination of characteristics: whereas 'ORAlodsem' bears double flowers (about 21 to 29 petals) of burgundy purple striped with cream yellow coloration overlaid with a coral orange blush, the non-disseminated seedling bears very double flowers of orange coloration with significantly heavier petalage (about 35 to 40 petals). The new variety is classified as a Climbing rose with a spreading climbing growing habit with canes about 300 cm. to about 350 cm. in length, whereas the pollen parent is classified as a Hybrid Tea rose with a significantly shorter upright growing habit (about 110 cm. in height).

COMPARISON WITH THE CLOSEST COMMERCIALLY AVAILABLE CULTIVAR

The new variety may be distinguished from its closest commercially available cultivar, 'MACoranlem' (U.S. Plant Pat. No. 9,191) by the following combination of characteristics: whereas 'ORAlodsem' bears double flowers (about 21 to 29 petals) of burgundy purple striped with cream yellow coloration overlaid with a coral orange blush, 'MACoranlem' bears double flowers of striped orange & yellow coloration with significantly heavier petalage (about 32 to 38 petals). The new variety is classified as a Climbing rose with a spreading climbing growing habit with canes about 300 cm. to about 350 cm. in length, whereas the closest commercially available cultivar is classified as a Shrub rose with a spreading significantly shorter growing habit (about 180 to about 250 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of December.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of December. Phenotypic expression may vary with environmental, cultural and climatic conditions, as well as differences in conditions of light and soil.

FLOWER

The new variety sometimes bears its flowers singly, usually in clusters of two to five per stem. Flowers may be borne in regular rounded clusters on strong somewhat short to medium length stems (about 26 to about 60 cm.). Outdoors, the plant blooms abundantly and nearly continuously during the growing season. The flowers have a moderate fruity to apple-like fragrance.

BUD

The peduncle is about 3.4 to about 5.1 cm. in length, of somewhat slender caliper (about 0.2 to about 0.3 cm. in diameter), and usually erect. It is smooth with many hairs. Peduncle color is between 146C and 146B often heavily suffused, especially on the side exposed to the sun, with between 187B and 187A.

Before the calyx breaks, the bud is about 1.2 to about 1.5 cm. in diameter at the widest point, about 1.8 to about 2.2 cm. in length, and pointed to somewhat ovoid in shape. The surface of the bud bears between 10 to 12 foliaceous appendages with some stipitate glands and hairs, usually with slender entire foliaceous parts extending beyond the tip of the bud about ¼ or more of its length. Bud color is between 137B and 137A often heavily suffused, especially on the side exposed to the sun, with near 187A.

The sepals are about 2.7 to about 3.4 cm. in length and about 0.8 to about 1.2 cm. in width at the widest point. The outer surface color of the sepal is between 137B and 137A often heavily suffused, especially on the side exposed to the sun, with near 187A. The outer surface of the sepal is moderately rough and bears between 0 to 6 foliaceous appendages with some stipitate glands and hairs. The inner surface color of the sepal is near 146D broadly bordered by near 137B. After the sepals open, the inner surface color is sometimes moderately suffused, especially on the area exposed to the sun, with between 187A and 187B. The inner surface of the sepal is covered with fine wooly tomentum; sepal margins are lined with few stipitate glands and many hairs.

The receptacle of the flower is of moderately long length (about 0.8 to about 1.1 cm.) and average in caliper (about 0.8 to about 1.2 cm. in diameter). The receptacle is cup-shaped in form. Its surface is smooth with thick fleshy walls. The receptacle color is between 144A and 146C often moderately suffused, especially on the side exposed to the sun, with between 187B and 187A.

As the petals open (after the calyx breaks), the bud is about 1.6 to about 1.9 cm. in diameter at the widest point, about 2.0 to about 2.6 cm. in length, and moderately ovoid in form. The color of the under surfaces of the newly opened petals is irregularly striped and flecked with as dark as between 53B and 47A to as light as between 11B and 10B sometimes moderately suffused with between 187C and 53A to as dark as between 187A and 187B. At the point where the petal attaches, there is a large zone of between 1C and 154C. The color of the upper surfaces of the newly opened petals is irregularly striped and flecked with as dark as between 187A and 187B to as light as between 10C and 11B sometimes moderately suffused with between 46B and 45A. At the point where the petal attaches, there is a large zone of between 2B and 1A.

BLOOM

When fully open, the bloom ranges from about 7.4 to about 10.4 cm. in diameter. Petalage is double with about 21 to 29 petals and about 2 to 12 petaloids irregularly arranged. When partially open, the bloom form is moderately high centered to somewhat cupped, and the petals are somewhat tightly spiraled to cupped with petal edges somewhat reflexed outward. When fully open, the bloom form is more cupped, and the petals are loosely cupped to somewhat undulated with petal edges moderately reflexed outward.

PETALS

The substance of the petals is heavy and of moderately thick thickness, with upper surfaces moderately satiny to somewhat velvety and under surfaces slightly shiny. The petals are about 4.2 to about 5.1 cm. in length and about 2.8 to about 5.4 cm. in width at the widest point. Petal margins are entire.

The outer petals are moderately obovate to somewhat rounded in shape with rounded apices.

The inner petals are obovate in shape with rounded apices.

Petaloids are about 0.8 to about 4.3 cm. in length and about 0.5 to about 4.0 cm. in width at the widest point. Petaloids are irregularly shaped moderately oblanceolate to somewhat subulate with rounded apices.

NEWLY OPENED FLOWER

The under surface color of the outer petals is irregularly striped and flecked with as dark as between 53B and 53C to as light as between 155B and 11C sometimes moderately suffused with between 53C and 60C. At the point where the petal attaches, there is a large zone of near 4B. The upper surface color of the outer petals is irregularly striped and flecked with as dark as between 187C and 59A to as light as between 155B and 11C sometimes moderately suffused with between 50A and 47B. At the point where the petal attaches, there is a large zone of between 4A and 3B.

The under surface color of the intermediate and inner petals is irregularly striped and flecked with as dark as between 53B and 53C to as light as between 4C and 11C sometimes lightly suffused with between 53C and 53D. The upper surface color of the intermediate and inner petals is irregularly striped and flecked with as dark as between 187B and 59A to as light as between 5D and 11C sometimes lightly suffused with between 50A and 47B.

The under and upper surface colors of the petaloids are similar in coloration to the upper and under surfaces of the intermediate and inner petals.

The general tonality of the newly opened flower is irregularly striped and flecked with as dark as between 187B and 59A to as light as between 5D and 11C.

THREE-DAY-OLD FLOWER

The under surface color of the outer, intermediate and inner petals is irregularly striped and flecked with as dark as between 53C and 53D to as light as between 155B and 155D sometimes moderately suffused with between 53C and 60C. At the point where the petal attaches, there is a large zone of between 155B and 155D. The upper surface color of the outer, intermediate and inner petals is irregularly striped and flecked with as dark as between 187B and 59A to as light as between 155B and 155D often moderately suffused with between 50A and 47B. At the point where the petal attaches, there is a large zone of between 155A and 155C.

The under and upper surface colors of the petaloids are similar in coloration to the upper and under surfaces of the intermediate and inner petals.

The general tonality of the three-day-old flower is irregularly striped and flecked with as dark as between 187B and 59A to as light as between 155B and 155D often moderately suffused with between 50A and 47B.

On the spent bloom, the petals usually drop off cleanly.

In December in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 155) and are arranged regularly about the pistils; a few are mixed with petaloids or tucked in the calyx. The filaments are of somewhat short to medium length (about 0.6 to about 0.9 cm.) most with anthers. Filaments are between 6A and 7A in color. The anthers are moderately small for the class and all open approximately at the same time. Anther color when immature is near 22A on the external part and near 11D on the internal part. Anther color at maturity is near 163A on the external part and near 200A on the internal part. Pollen is moderate and between 18C and 19C in color.

FEMALE REPRODUCTIVE ORGANS

Pistils vary in number (average about 95). The styles are somewhat uneven, short to average in length (about 0.3 to about 0.7 cm.), moderately heavy in caliper, and loosely bunched to somewhat separated. Stigma color is between 8B and 10B. Style color is near 4D often heavily suffused with between 53A and 53B. Ovaries are usually all enclosed in the calyx.

Hips have not been observed on this variety when grown in Pomona, Calif.

FOLIAGE

The compound leaves are usually comprised of three to seven leaflets and are borne abundantly. The seven-leaflet leaves are about 12.6 to about 23.1 cm. in length and about 9.4 to about 18.7 cm. in width at the widest point, moderately leathery to somewhat crisp in texture, and very glossy in finish on the upper side and matte to slightly glossy in finish on the underside. The leaves have a pinnate venation pattern. The terminal leaflets are about 5.0 to about 10.3 cm. in length and about 3.3 to about 6.1 cm. in width at the widest point, shaped moderately ovate to somewhat oval with acuminate to somewhat acute apices and rounded bases. Their margins are usually simply serrate.

The upper surface color of the mature leaf is between 137A and 147A. The under surface color of the mature leaf is between 147B and 146A. The under and upper colors of the leaf veins on the mature leaf are similar in coloration to the upper and under surfaces colors of the mature leaf. The upper surface color of the young leaf is near 137A, often heavily suffused with between 187A and 187B. The under surface color of the young leaf is near 138B, often heavily suffused with between 187B and 187A. The under and upper colors of the leaf veins on the young leaf are similar in coloration to the upper and under surfaces colors of the young leaf.

The rachis is moderately heavy in caliper and rough. The upper side is deeply grooved with some stipitate glands on the edges of the grooves. The underside of the rachis is rough with some stipitate glands and few small prickles. The rachis color is near 146D on the underside and near 146B on the upper side often moderately suffused on the young leaves with between 187A and 187B.

The stipules are about 1.2 to about 2.5 cm. in length and moderately wide (about 0.5 to about 0.8 cm.) with somewhat long straight points that usually turn out at an angle of more than 45 degrees and sometimes recurve toward the stem. The under and upper surface color of the stipule is between 137A and 137B.

The petiole is moderately heavy in caliper and rough. The upper side is deeply grooved with some stipitate glands on the edges of the grooves. The underside of the petiole is rough with some stipitate glands and few small prickles. The petiole is about 0.7 to about 2.4 cm. in length and about 0.1 to about 0.2 cm in width at the widest point. The petiole color is near 146D on the underside and near 146B on the upper side often moderately suffused on the young leaves with between 187A and 187B.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a spreading climbing growing habit with canes about 300 cm. to about 350 cm. in length with full branching. It displays very vigorous growth and the canes are of medium caliper for the class (about 1.8 to about 2.7 cm. in diameter at the widest point).

The color of the major stems is near 147B often moderately suffused, especially on the side exposed to the sun, with near 177B. They bear many large prickles that are about 1.0 to about 1.3 cm. in length. The large prickles are angled moderately to somewhat hooked downward with a moderately short to medium length broad oval base; prickle color is between 200D and 165A. The major stem bears several small prickles of similar shape and coloration.

The color of the branches is between 146B and 146C often moderately suffused, especially on the side exposed to the sun, with between 187B and 187A. They bear some large prickles which are of similar shape to the large prickles on the major stems. The prickles are about 0.4 to about 0.6 cm. in length. Prickle color is between 200A and 165A. The branches bear several small prickles of similar shape and coloration.

The color of the new shoots is between 146B and 146C often moderately suffused with between 187A and 187B. They bear some large prickles which are of similar shape to the large prickles on the major stems. The prickles are about 0.6 to about 0.9 cm. in length. Prickle color is near 152B often heavily suffused with between 187A and 187B. The shoots bear several small prickles of similar shape and coloration.

I claim:

1. A new and distinct Climbing rose plant of the variety substantially as described and illustrated herein.

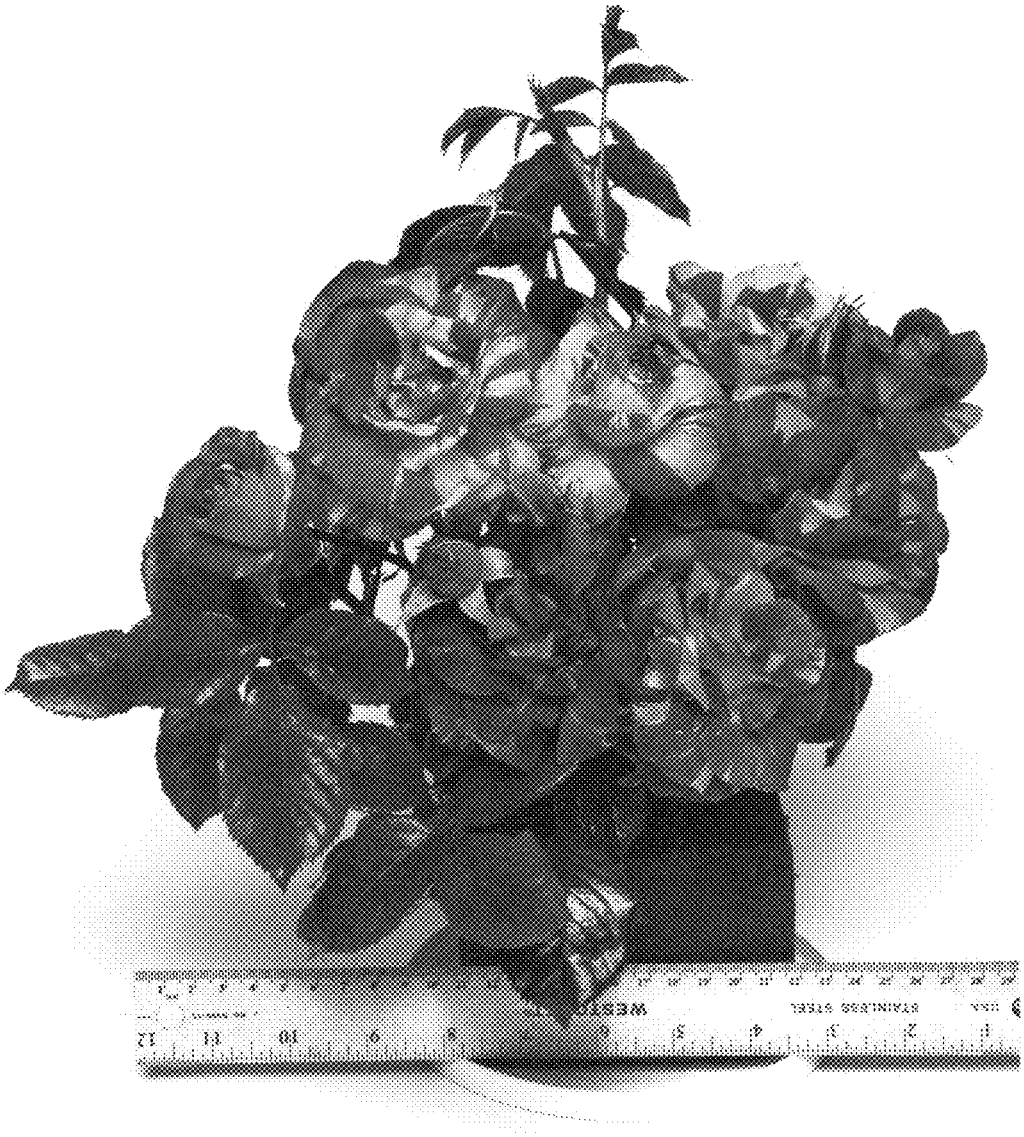

* * * * *